United States Patent [19]

Brown et al.

[11] Patent Number: 4,959,071
[45] Date of Patent: Sep. 25, 1990

[54] PARTIALLY STABILIZED KNEE PROSTHESIS

[75] Inventors: David R. Brown; Jeff L. Martin, both of Warsaw, Ind.

[73] Assignee: Biomet, Inc., Warsaw, Ind.

[21] Appl. No.: 305,713

[22] Filed: Feb. 3, 1989

Related U.S. Application Data

[63] Continuation-in-part of Ser. No. 151,659, Feb. 3, 1988, Pat. No. 4,892,547.

[51] Int. Cl.$^5$ .............................................. A61F 2/38
[52] U.S. Cl. ................................................... 623/20
[58] Field of Search ................... 623/11, 18, 20, 21, 623/22, 23

[56] References Cited

U.S. PATENT DOCUMENTS

| | | | |
|---|---|---|---|
| 3,728,742 | 4/1973 | Averill et al. | 623/20 |
| 3,774,244 | 11/1973 | Walker | 623/20 |
| 3,840,905 | 10/1974 | Deane . | |
| 4,209,861 | 7/1980 | Walker et al. | 623/20 |
| 4,213,209 | 7/1980 | Insall et al. | 623/20 |
| 4,216,549 | 8/1980 | Hillberry et al. | 623/20 |
| 4,257,129 | 3/1981 | Volz | 623/20 |
| 4,268,920 | 5/1981 | Engelbrecht et al. | 623/20 |
| 4,298,992 | 11/1981 | Burstein et al. | 623/20 |
| 4,309,778 | 1/1982 | Buechel et al. | 623/20 |
| 4,340,978 | 7/1982 | Buechel et al. | 623/20 |
| 4,404,691 | 9/1983 | Buning et al. | 623/20 |
| 4,470,158 | 9/1984 | Pappas et al. | 623/20 |
| 4,479,271 | 10/1984 | Bolesky et al. | 623/20 |
| 4,487,203 | 12/1984 | Androphy | 128/303 R |
| 4,524,766 | 6/1985 | Petersen | 128/92 VW |
| 4,567,885 | 2/1986 | Androphy | 128/92 R |
| 4,578,081 | 3/1986 | Harder et al. | 623/22 |
| 4,586,933 | 5/1986 | Shoji et al. | 623/20 |
| 4,634,444 | 1/1987 | Noiles | 623/20 |
| 4,646,729 | 3/1987 | Kenna et al. | 128/92 VW |
| 4,653,488 | 3/1987 | Kenna | 128/92 VW |
| 4,673,407 | 6/1987 | Martin | 623/20 |
| 4,714,473 | 12/1987 | Bloebaum | 623/20 |

FOREIGN PATENT DOCUMENTS 2568467 of 1986 France .
294298 12/1988 France ............................ 623/20
0664686 3/1988 Switzerland ..................... 623/18
2067412 7/1981 United Kingdom .

OTHER PUBLICATIONS

"The Posterior Stabilized Condylar Prosthesis: A Modification of a Total Condylar Design," Journal of Bone and Joint Surgery, J. N. Insall et al., vol. 64-A, No. 9, pp. 1317–1323, Dec. 1982.

Primary Examiner—Richard J. Apley
Assistant Examiner—Howard Flaxman
Attorney, Agent, or Firm—Barnes & Thornburg

[57] ABSTRACT

A knee joint prosthesis includes a femoral component having spaced condylar bearing portions, an anterior intercondylar portion, a posterior intercondylar portion, an intercondylar opening, and a tibial component having spaced bearing surfaces for supporting the bearing portions of the femoral component, and a relatively low intercondylar eminence between the bearing surfaces. The eminence has a peak which defines the highest portion of the tibial component, as measured relative to the tibial plateau. The peak extends into, but not through, the intercondylar opening, such that resection of the femur to provide clearance for the opening and the eminence is not required. The tibial component comprises a base and insert. The insert is preferably a non-metallic pad having the bearing surfaces and eminence formed on a superior surface thereof. The base has a platform for supporting the insert, and a downwardly extending portion for insertion into an opening in the tibia to secure the platform to the tibial plateau. The exterior surface of the posterior intercondylar portion of the femoral component has a longitudinally extending ridge or runner midway between the condylar bearing portions. The intercondylar eminence of the tibial component has a corresponding groove which extends generally parallel to the spaced bearing surfaces. When the knee flexes, the femoral and tibial component rotate with respect to each other and the runner of the femoral component rotatably slides in the groove of the tibial component, coacting to reduce anterior movement of the femoral component.

14 Claims, 5 Drawing Sheets

PARTIALLY STABILIZED KNEE PROSTHESIS

SUMMARY OF THE INVENTION

This is a continuation-in-part application of U.S. Ser. No. 151,659, filed Feb. 3, 1988, now U.S. Pat. No. 4,892,54 entitled "Partially Stabilized Knee Prosthesis."

The present invention relates generally to knee joint prostheses and, more particularly, to a knee joint prosthesis which provides for partial stabilization of the joint during leg flexion, while minimally constraining "natural" movements of the joint, and while requiring no additional resection of the femur as compared to non-stabilized knee joint prostheses of similar design.

Knee joint prostheses, which have been generally available for a number of years, can be classified into two types. The first type has been referred to as "stabilized" prostheses in which hinge or ball and socket type joints are used as substitutes for the anatomical knee joint In this type of joint, movement of the knee is controlled and constrained by the hinge pin or ball and socket, and little reliance is placed on the surrounding soft tissues (i.e., tendons and ligaments) to stabilize the joint. These joints allow little, if any, anterior-posterior translation, lateral angulation, or rotation, as does the anatomical knee joint. For this reason, such joints are considered to be undesirable, and may be prone to premature failure.

The other type of knee joint prosthesis is generally referred to as a "condylar surface" prosthesis. In this type of joint, the respective bearing surfaces on the femur and tibia are replaced by similarly shaped and positioned prosthetic bearing surfaces, which are separate from and not directly connected to each other This type of joint relies upon the surrounding tendons and ligaments to hold the joint together and to impart stability to the joint during movements. These joints are relatively light in weight, afford substantial rotational and translational freedom of movement, and require relatively minor resection of the natural bone and disturbances of the surrounding soft tissues during implantation. Examples of these types of prosthetic joints are disclosed in U.S. Pat. Nos. 3,728,742 and 3,774,244.

In situations where the tendons and ligaments surrounding the knee are damaged or are otherwise unable to impart the desired degree of stability to the condylar surface type prostheses, attempts have been made to introduce features which impart some degree of stability to the joint (by virtue of interactions between the joint components), while minimally interfering with the "natural" rotational and translational freedom of movement of the joint. Examples of devices which include features directed to this end are shown in U.S. Pat. Nos. 4,209,861; 4,213,209 and 4,298,992. Each of the devices described in these patents include a tibial component which has a spaced pair of concave bearing surfaces, and a femoral component which has a spaced pair of convex condylar bearing portions which are matingly received and supported by the concave bearing surfaces of the tibial component. The tibial component further has an upwardly extending post located between the bearing surfaces which extends into a box-like recess formed between the condylar bearing portions of the femoral component. In each case, the box-like recess has lateral side walls, anterior and posterior walls, and a superior wall which interact with (i.e., contact) the post of the tibial component under certain conditions to restrain relative movements of the tibial and femoral components within desired limits While such designs have been successful in imparting a degree of stability to this type of joint, the existence of the box-like recess in the femoral component requires resection of a greater amount of natural bone from the femur, and requires a more complicated preparation procedure for the femur prior to implantation. Furthermore, interactions between the tibial post and the surfaces of the femoral box, which take place at a point which is relatively high above the tibial plateau, increase the tipping moment applied to the tibial component of the joint, and can lead to early loosening and failure of the joint. Accordingly, there exists a need for an improved, partially stabilized knee joint prosthesis which retains the freedom of movement characteristic of the anatomical knee joint, which imparts some degree of stability against anterior dislocations of the femur during leg flexion, which is relatively simple to implant, and which requires minimal removal of the natural bone of the femur.

It is an object of this invention to provide an improved knee joint prosthesis which offers the above-noted advantages.

These and other objects are attained in a knee joint prosthesis which comprises a femoral component and a tibial component which are adapted for implantation on the condylar end of the femur and the tibial plateau, respectively. The femoral component has a pair of spaced-apart condylar bearing portions, an anterior intercondylar portion, a posterior intercondylar portion, and an intercondylar opening defined by lateral, posterior, and anterior edges of the condylar bearing portions, the anterior intercondylar portion, and the posterior intercondylar portion, respectively. The edges which define the intercondylar opening are substantially coplanar such that a box-like recess or structure extending into the intercondylar portion of the femur is not formed (or required) by the joint of the present invention. The tibial component has a pair of spaced-apart bearing surfaces for supporting the condylar bearing portions of the femoral component, and a relatively low intercondylar eminence disposed between the bearing surfaces. The intercondylar eminence has a posterior surface and a peak which defines the highest portion of the tibial component, as measured relative to the tibial plateau. The peak of the intercondylar eminence extends into, but not through, the intercondylar opening in the femoral component, such that resection of the femur to provide clearance for the intercondylar opening and the intercondylar eminence is not required. In a preferred embodiment, an anterior edge of the posterior intercondylar portion of the femoral component contacts the posterior side of the intercondylar eminence after the knee joint has flexed through a substantial portion of its range of flexion to prevent anterior dislocation of the femoral component, relative to the tibial component, as the degree of flexion increases. In an especially preferred embodiment, contact between the edge of the posterior intercondylar portion and the posterior side of the intercondylar eminence occurs after the joint has flexed through approximately 40° of its range of flexion.

As flexion continues beyond the point where the edge of the posterior intercondylar portion contacts the side of the intercondylar eminence, an exterior side, or guide surface, of the posterior intercondylar portion contacts the posterior side of the intercondylar eminence to cause the condylar bearing portions to roll posteriorly on the bearing surfaces of the tibial component. This results in displacement of the point of contact between each bearing portion and its respective bearing surface posteriorly by a predetermined distance. In a preferred embodiment, posterior displacement of this point of contact begins after flexion of the knee joint through approximately 40°, and ends after flexion of the joint through approximately 90°.

The shape of the resected femur (i.e., the distal cut) conforms to contours which match respective interior surfaces of the condylar bearing portions and the anterior and posterior intercondylar portions of the femoral component. These surfaces are preferably substantially flat, planar surfaces which intersect the substantially coplanar edges of these portions which define the intercondylar opening. Accordingly, the profile of the distal cut is essentially unchanged by the existence of the intercondylar opening in the femoral component, and by the presence of the intercondylar eminence on the tibial component.

In a preferred embodiment of the knee joint of the present invention, the tibial component comprises a tibial base and a tibial insert. The insert is preferably a non-metallic pad having the spaced-apart bearing surfaces and the intercondylar eminence formed on its superior surface. The base comprises a substantially planar platform portion for supporting the tibial insert, and a downwardly extending extension portion for insertion into an opening in the tibia to anchor or secure the platform portion to the tibial plateau. In an especially preferred embodiment, at least a portion of the extension portion is detachably secured to the platform.

A preferred embodiment of the knee joint of the present invention further comprises fastening means for securing the tibial insert to the tibial base, and for securing the detachable extension portion to the tibial platform. In an especially preferred embodiment, a single screw accomplishes both of these functions. The tibial platform may also be provided with one or more laterally spaced openings for receiving additional fasteners (e.g., bone screws) to aid in securing the platform portion to the tibial plateau. When a non-symmetrical detachable extension portion is used, means may be provided to rotationally orient the detachable extension portion, relative to the platform portion.

In another preferred embodiment of the invention, the exterior surface of the posterior intercondylar portion of the femoral component has a ridge or runner extending along it parallel to and generally midway between the pair of spaced-apart condylar bearing portions. The tibial component has a corresponding groove therein which runs in the intercondylar eminence between and parallel to the spaced-apart bearing surfaces of the tibial component. When the knee flexes, the femoral and tibial component rotate with respect to each other and the runner of the tibial component rotatably slides in the groove of the tibial component. The ridge of the femoral component and the groove of the tibial component coact to reduce any anterior movement of the femoral component when the knee flexes. In contrast to the first described embodiment, the configuration of the tibial component is such that the femoral component is not moved posteriorly as the knee flexes. Rather than rotating and then rolling on the tibial component, the femoral component only rotates on the tibial component. Also, although this second embodiment is described in the detailed description with the femoral component having the ridge and the tibial component having the groove, the location of the ridge and groove can be reversed so that the femoral component has the groove and the tibial component has the ridge. Further with regard to this second embodiment, in a preferred embodiment the tibial component also comprises a tibial base and a tibial insert wherein the tibial insert is preferably a non-metallic pad having the spaced-apart bearing surfaces and the intercondylar eminence formed in its superior surface with the groove formed in the intercondylar eminence.

Other objects, advantages and novel features of the present invention will become apparent from the following detailed description of the invention when considered in conjunction with the accompanying drawings.

DETAILED DESCRIPTION OF THE DRAWINGS

FIGS. 1-5 show side, top, front, rear, and bottom views of a femoral component 10 which is constructed in accordance with the principles of the present invention. For purposes of this discussion, the anterior side or direction is to the left in FIG. 1 and the posterior side or direction is to the right of FIG. 1. The anterior side of femoral component 10 is that side which forms the front of the knee joint when component 10 is implanted on the condylar end of the femur, and the posterior side of component 10 is that side which forms the back side of an implanted knee joint.

Femoral component 10 comprises a spaced-apart pair of downwardly convex bearing portions 12 which extend from the anterior side to the posterior side of component 10. The shapes of the outer surfaces of bearing portions 12 closely approximate the shapes of anatomical femoral condyles on the knee joint end of the femur Femoral component 10 further comprises a generally vertically oriented patellar guide portion 14 which serves as a guide for the movements of a natural or prosthetic patella. The interior contours of femoral component 10 (which closely match the exterior contour of the end of the femur after the femur has been prepared to receive femoral component 10, i.e., the distal cut) is defined by generally vertical surface 16 on the posterior side of patellar guide portion 14, by posteriorly downwardly angled surfaces 18, 22 and 20 of bearing portions 12 and anterior intercondylar portion 21, respectively, by generally horizontal surfaces 24 and 26 of bearing portions 12, by posteriorly upwardly angled surfaces 28, 32 and 30 of bearing portions 12 and posterior intercondylar portion 31, respectively, and by vertically extending surfaces 34, 38 and 36 of bearing portions 12 and posterior intercondylar portion 31, respectively.

Surface 16 defines the posterior surface of patellar guide portion 14 and extends across substantially the entire width of femoral component 10. Opposing anterior surface 40 of patellar guide portion 14 is especially shaped to allow anatomical tracking of the patella, and may differ slightly in shape depending upon whether component 10 is intended for use on the right or left femur. Alternatively, the same shape for surface 40 may be used in either application.

Figure 1:
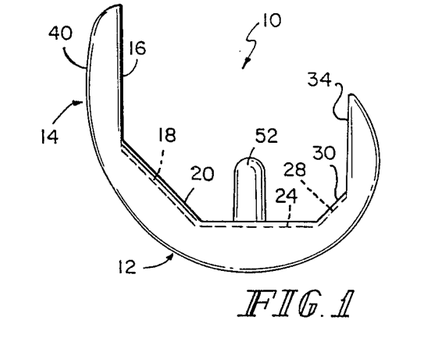
FIG. 1 shows a side view of a femoral component of a knee joint formed in accordance with the present invention.
Figure 2:
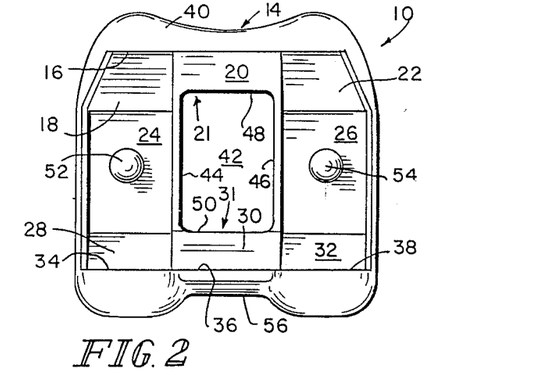
FIG. 2 shows a top plan view of the femoral component of FIG. 1.
Figure 3:
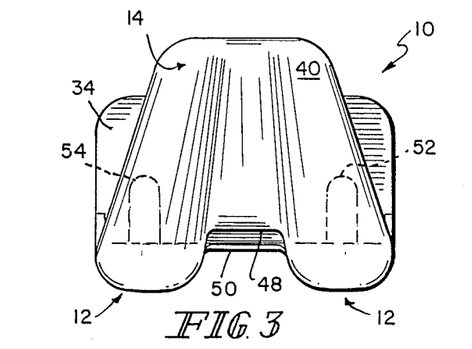
FIG. 3 shows a front or anterior view of the femoral component of FIGS. 1 and 2.
Figure 4:
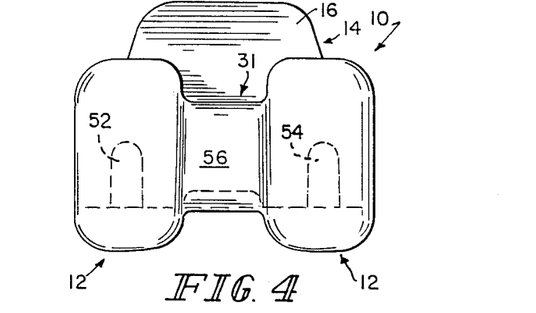
FIG. 4 shows a rear or posterior view of the femoral component of FIGS. 1-3.
Figure 5:
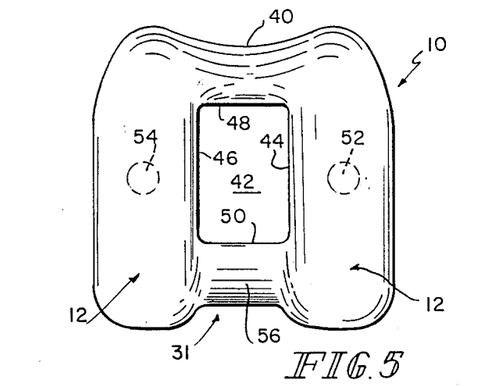
FIG. 5 shows a bottom plan view of the femoral component of FIGS. 1-4.
Figure 6:
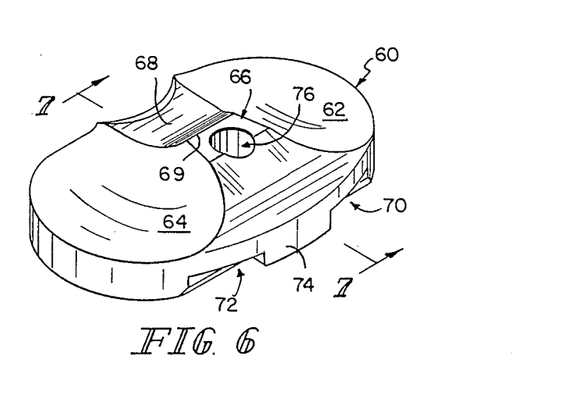
FIG. 6 shows a perspective view of a tibial insert formed in accordance with the present invention.

Surfaces 18 and 22 oppose anterior portions of condylar bearing portions 12, respectively. Surfaces 24 and 26 oppose central portions of condylar bearing portions 12, while surfaces 28 and 34, and 32 and 38 oppose respective posterior portions of condylar bearing portions 12. Surface 20 is an interior surface of an anterior intercondylar portion 21 which extends between the anterior portions of condylar bearing portions 12. Surface 20 may be slightly raised, as compared to surfaces 18 and 22, as shown in FIG. 1. Surfaces 30 and 36 are interior surfaces of posterior intercondylar portion 31 which extends between respective posterior portions of condylar bearing portions 12. Opposing interior surfaces 30 and 36 of posterior intercondylar portion 31 is exterior surface 56.

Component 10 further comprises an intercondylar opening 42 which is defined by lateral edges 44 and 46 of condylar bearing portions 12, posterior edge 48 of anterior intercondylar portion 21, and anterior edge 50 of posterior intercondylar portion 31. These edges lie in substantially the same horizontal, or slightly convex, plan (as viewed in FIG. 1), such that no portion of the edges which form the side walls of opening 42 extend inwardly toward the femur beyond the interior surfaces of condylar bearing portions 12 and the other interior surfaces which define the contour of the distal cut. Accordingly, no additional resection of the femur is required to accommodate a femoral component which incorporates this feature Femoral component 10 further comprises upwardly extending cylindrical posts 52 and 54 which fit into holes formed in the distal end of the femur to aid in firmly attaching component 10 to the femur. Femoral component 10 is preferably formed of a biologically compatible metal, such as a cobalt-chromium alloy or a titanium alloy.

FIGS. 6-11 show an assortment of views of tibial insert 60 of the present invention. Tibial insert 60 is preferably constructed of a biologically compatible high density polymer, such as ultra-high molecular weight polyethylene (UHMWPE).

Tibial insert 60 has two spaced-apart upwardly concave bearing surfaces 62 and 64 which will provide support for, and which will be in contact with, condylar bearing portions 12 of femoral component 10 in the implanted joint. In addition to bearing surfaces 62 and 64, the top surface of tibial insert 60 is provided with a relatively low intercondylar eminence 66 disposed between bearing surfaces 62 and 64, and a generally arcuately shaped (in cross-section) guide surface 68 on a posterior side of intercondylar eminence 66. In a preferred embodiment of the invention, guide surface 68 has a partial circular shape in cross-section, and has a radius R of approximately 0.5" (see FIG. 7). Guide surface 68 extends upwardly along the posterior side of eminence 66 to a peak 69 which defines the highest portion of the tibial insert and which, when extended tangentially, forms an angle A of approximately 37° with the horizontal.

Tibial insert 60 has two notches 70 and 72 formed in the lower portion of anterior surface 74. Notches 70 and 72 mate with projections 94 and 96 on tibial base 90, described in detail below, to locate and help secure tibial insert 60 on and to tibial base 90.

Figure 7:
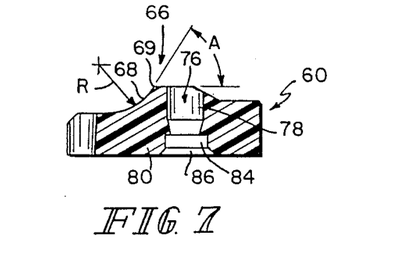
FIG. 7 shows a sectional view of the tibial insert of FIG. 6 taken along section line 7—7.
Figure 8:
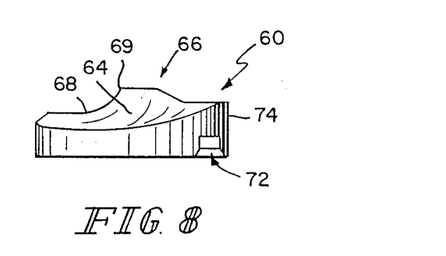
FIG. 8 shows a side view of the tibial insert of FIGS. 6 and 7.
Figure 9:
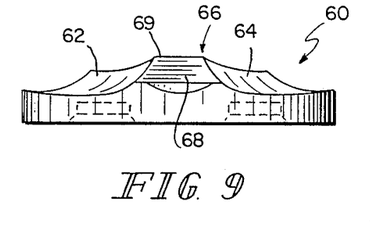
FIG. 9 shows a rear or posterior view of the tibial insert of FIGS. 6-8.
Figure 10:
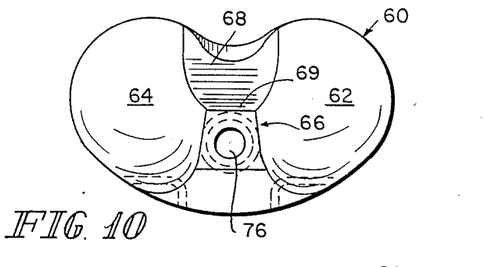
FIG. 10 shows a top plan view of the tibial insert of FIGS. 6-9.
Figure 11:
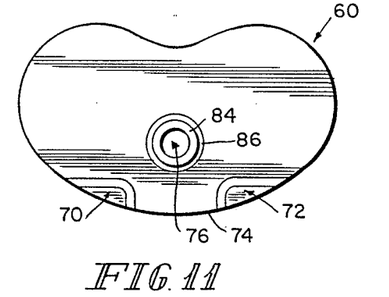
FIG. 11 shows a bottom plan view of the tibial insert of FIGS. 6-10.
Figure 16:
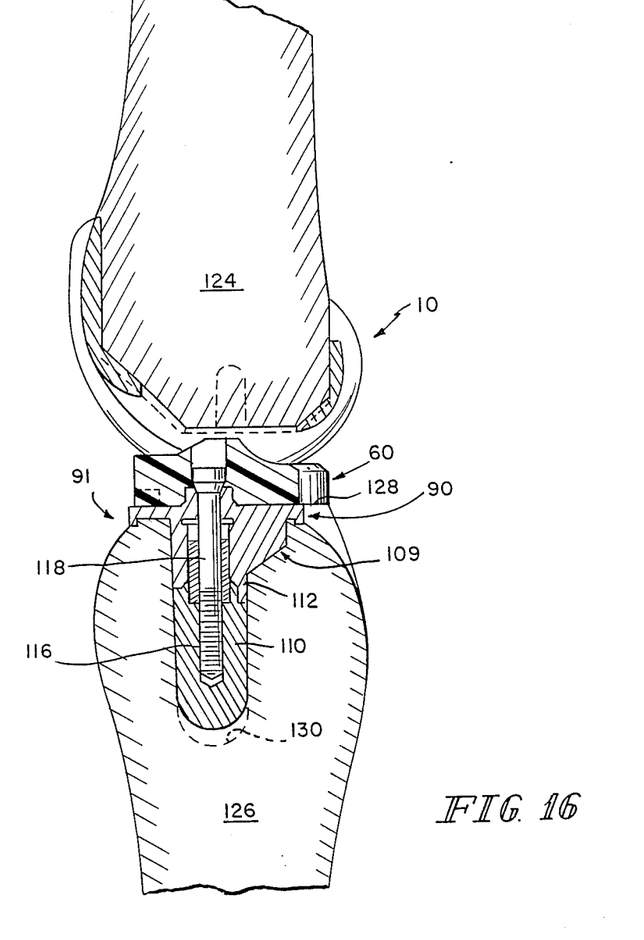
FIG. 16 shows a sectional view of the knee joint of the present invention after the femoral component and the tibial base and insert have been attached to the femur and tibia, respectively.

Tibial insert 60 further comprises an opening 76 having a cross-section which is best illustrated in FIG. 7. Moving from the top of tibial insert 60 toward the bottom, opening 76 has a first generally cylindrical portion 78, an inwardly tapered portion 80, enlarged cylindrical portion 84, and outwardly tapered portion 86. Portions 78 and 80 are intended to receive the head of a screw which holds insert 60 to tibial base 90, as is illustrated in FIG. 16. Portions 84 and 86 receive an upwardly extending projection 100 on tibial base 90, which is illustrated in FIG. 14.

Figure 12:
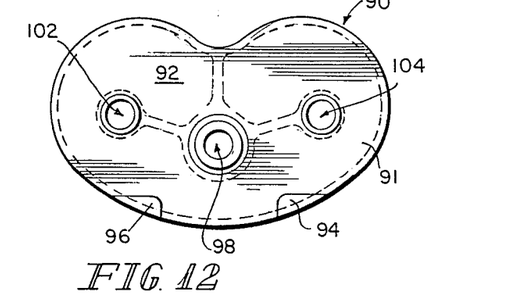
FIG. 12 shows a top plan view of a tibial base formed in accordance with the present invention.

FIG. 12 shows a top view of tibial base 90. Base 90 comprises a generally planar platform 91 having a top surface 92 and a bottom surface 108 Top surface 92 of tibial base 90 is generally flat, except for two upwardly extending projections 94 and 96 located on an anterior edge of platform 91 Projections 94 and 96 mate with notches 70 and 72, respectively, of tibial insert 60 when insert 60 is positioned on surface 92. A central opening 98 is formed in base 90 and is coaxially aligned with opening 76 in insert 60 when insert 60 is placed on surface 92 of base 90. An upwardly extending projection 100 (FIG. 14) surrounds opening 98 and is received in portions 84 and 86 of opening 76 when insert 60 is supported by base 90. Platform 91 also has laterally spaced through holes 102 and 104 which receive optional bone screws to aid in securing base 90 to the end of the resected tibial plateau The upper portions of holes 102 and 104 are countersunk so that the heads of the optional bone screws fit entirely below the level of surface 92.

Figure 13:
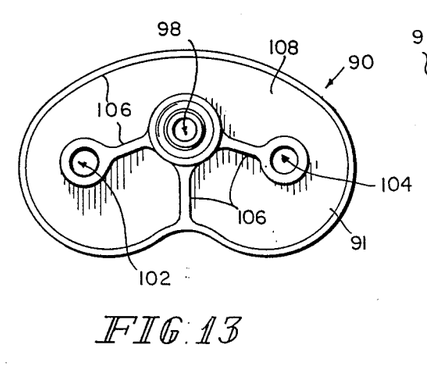
FIG. 13 shows a bottom plan view of the tibial base of FIG. 12.

FIG. 13, which shows a plan view of the bottom of tibial base 90. FIG. 13 illustrates the pattern of reinforcing ribs 106 which extends around the outer periphery of bottom surface 108 of platform 91 and which connects and surrounds the outer periphery with each of the openings 98, 102 and 104.

Figure 14:
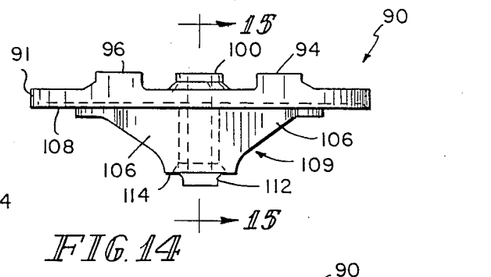
FIG. 14 shows a front view of the tibial base of FIGS. 12 and 13.
Figure 15:
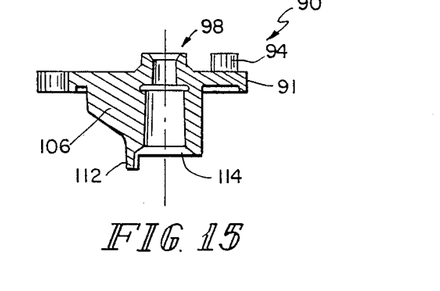
FIG. 15 shows a sectional view of the tibial base of FIGS. 12-14, taken along line 15—15 in FIG. 14.

FIG. 14 shows a front view of tibial base 90, including platform 91 and downwardly extending portion 109. A detachable extension 110 (see FIG. 16) attaches to downwardly extending portion 109 which, along with extension 110, fits into an opening formed in the tibial plateau to secure base 90, and insert 60, to the tibia. A locating tab 112 extends downwardly from lower surface 114 of portion 109 for rotationally orienting extension 110 relative to the base. As best illustrated in FIG. 16, extension 110 is secured to base 90 by screw 118 which extends through opening 98 and into an opening (which may be threaded) in extension 110. FIG. 15 shows a sectional view of the preferred embodiment of tibial base 90, taken along line 15—15 in FIG. 14.

FIG. 16 shows a sectional view of femoral component 10, tibial insert 60, tibial base 90, and extension 110 in place on resected femur 124 and tibia 126 Base 90 is positioned on a flattened plateau 128, with extension 110 extending downwardly into an opening 130 formed in the tibia. If additional stability is desired, extension 110 may be replaced with a longer, but otherwise similar, extension. If relative orientation of extension 110 is important, locating tab 112 can be used to orient extension 110, as desired, by providing a mating notch or flat in or on extension 110. Screw 118 extends through openings 76 and 98, and into opening 116 in extension 110 to secure the three parts together As previously noted, optional bone screws may be provided, if desired, through platform 91 and into tibia 126 to aid in securing base 90 to the tibia. In the event the joint must be replaced, screw 118 can be removed, and insert 60 can be replaced, with a new insert being attached by screw 118 to undisturbed base 90 and extension 110. Alternatively, extension 110 may be removed and replaced with a longer or otherwise larger extension, if necessary.

Femur 124 is resected to fit the contours defined by internal surfaces 16-38 of femoral component 10. Intercondylar eminence 66 of tibial insert 60 extends into, but not through, intercondylar opening 42 of femoral component 10. Peak 69 of eminence 66 remains below the level of surfaces 24 and 26, which intersect the lateral edges 44 and 46 of opening 42, so that additional removal of bone material from femur 124 is not necessary to provide clearance for eminence 66.

Figure 17A:
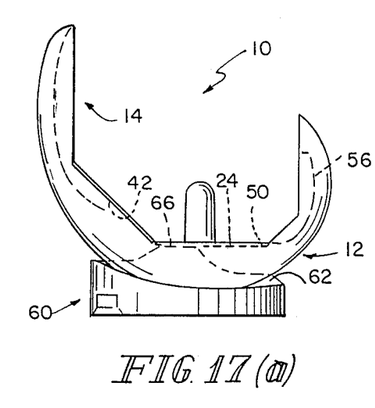
FIGS. 17(a), (b) and (c) show the femoral component and the tibial insert as positioned at full extension and at various points of flexion.
Figure 17B:
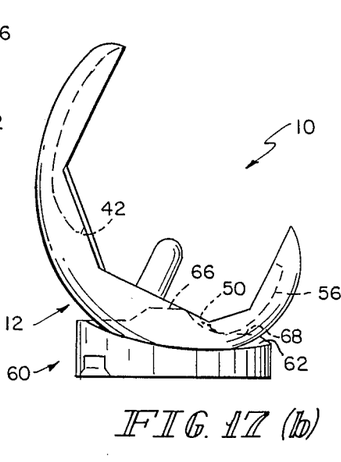
Figure 17C:
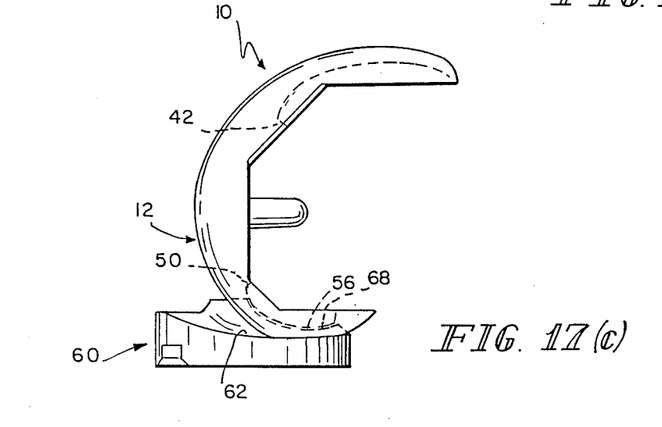

FIGS. 17(a), 17(b) and 17(c) illustrate the relative positions of femoral component 10 and tibial insert 60 when the knee joint is in the fully extended position (FIG. 17(a)), when the joint is flexed at approximately 40° flexion (FIG. 17(b)) and at approximately 90° flexion (FIG. 17(c)). In the fully extended position illustrated in FIG. 17(a), condylar bearing portions 12 of femoral component 10 rest against bearing surfaces 62 and 64 of tibial insert 60. Eminence 66 extends into opening 42, but remains below the level of generally horizontal surfaces 24 and 26 which intersect the lateral edges 44 and 46 of opening 42. In this position, the joint is minimally constrained by the contacting bearing surfaces of component 10 and insert 60, and is relatively free to move rotationally and translationally within limits imposed by the surrounding soft tissues.

FIG. 17(b) shows the relative positions of femoral component 10 and tibial insert 60 after flexion of the joint through approximately 40° from full extension. At this point, anterior edge 50 of posterior intercondylar portion 31 contacts guide surface 68 on the posterior side of intercondylar eminence 66 to constrain the movement of femoral component 10 anteriorly, relative to tibial insert 60. Edge 50 contacts guide surface 68 at a point which is relatively close, in vertical distance, to the points of attachment of tibial insert 60 and base 90 to the tibia, so that a relatively small tipping moment is produced as flexion continues.

After the initial contact between edge 50 and guide surface 68, exterior surface 56 of posterior intercondylar portion 31 contacts guide surface 68 and remains in contact with surface 68 as the degree of flexion increases. This contact restrains any tendencies femoral component 10 may have to move anteriorly, relative to tibial insert 60, which would result in sliding contact between condylar bearing portions 12 and bearing surfaces 62 and 64. Instead, bearing portions 12 "roll" posteriorly along bearing surfaces 62 and 64 for a predetermined displacement dictated by the contours of exterior surface 56 and guide surface 68.

FIG. 17(c) shows the relative positions of component 10 and insert 60 after flexion of the joint through approximately 90°. In this position, condylar bearing portions 12 are in load bearing contact with bearing components 62 and 64 in an area which is posteriorly displaced from the contact area between these load bearing surfaces when the joint is fully extended (i.e., as shown in FIG. 17(a)). Exterior surface 56 and guide surface 68 are preferably shaped such that further posterior displacement of the contact area (i.e., beyond the displacement reached at 90° flexion) does not occur as flexion continues. Thus, as the joint flexes from 90° to complete flexion (approximately 130°), condylar bearing portions 12 slide, rather than roll, on bearing surfaces 62 and 64.

FIGS. 18-21 show side, top, rear, and bottom views of a femoral component 210 of another embodiment of a partially stabilized knee prosthesis constructed according to the invention. For purposes of this discussion, the anterior side or direction is to the right in FIG. 18 and the posterior side or direction is to the left of FIG. 18. The anterior side of femoral component 210 is that side which forms the front of the knee joint when component 210 is implanted on the condylar end of the femur, and the posterior side of component 210 is that side which forms the back side of an implanted knee joint.

Femoral component 210 comprises a pair of spaced-apart downwardly convex bearing portions 212 which extend from the anterior side to the posterior side of femoral component 210. The shapes of the outer surfaces of bearing portions 212 closely approximate the shapes of anatomical femoral condyles on the knee joint end of the femur. Femoral component 210 further comprises a generally vertically oriented patellar guide portion 214 which serves as a guide for the movements of a natural or prosthetic patella. The interior contours of femoral component 210 (which closely match the exterior contour of the end of the femur after the femur has been prepared to receive femoral component 210, i.e., the distal cut) is defined by generally vertical surface 216 on the posterior side of patellar guide portion 214, by posteriorly downwardly angled surfaces 218, 222 and 220 of bearing portions 212 and anterior intercondylar portion 221, respectively, by generally horizontal surfaces 224 and 226 of bearing portions 212, by posteriorly upwardly angled surfaces 228, 232 and 230 of bearing portions 212 and posterior intercondylar portion 231, respectively, and by vertically extending surfaces 234, 238 and 236 of bearing portions 212 and posterior intercondylar portion 231, respectively.

Surface 216 defines the posterior surface of patellar guide portion 214 and extends across substantially the entire width of femoral component 210. Opposing anterior surface 240 of patellar guide portion 214 is especially shaped to allow anatomical tracking of the patella, and may differ slightly in shape depending upon whether component 210 is intended for use on the right or left femur. Alternatively, the same shape for surface 240 may be used in either application.

Figures 18, 19, 20, 21, 22, 23, 24:
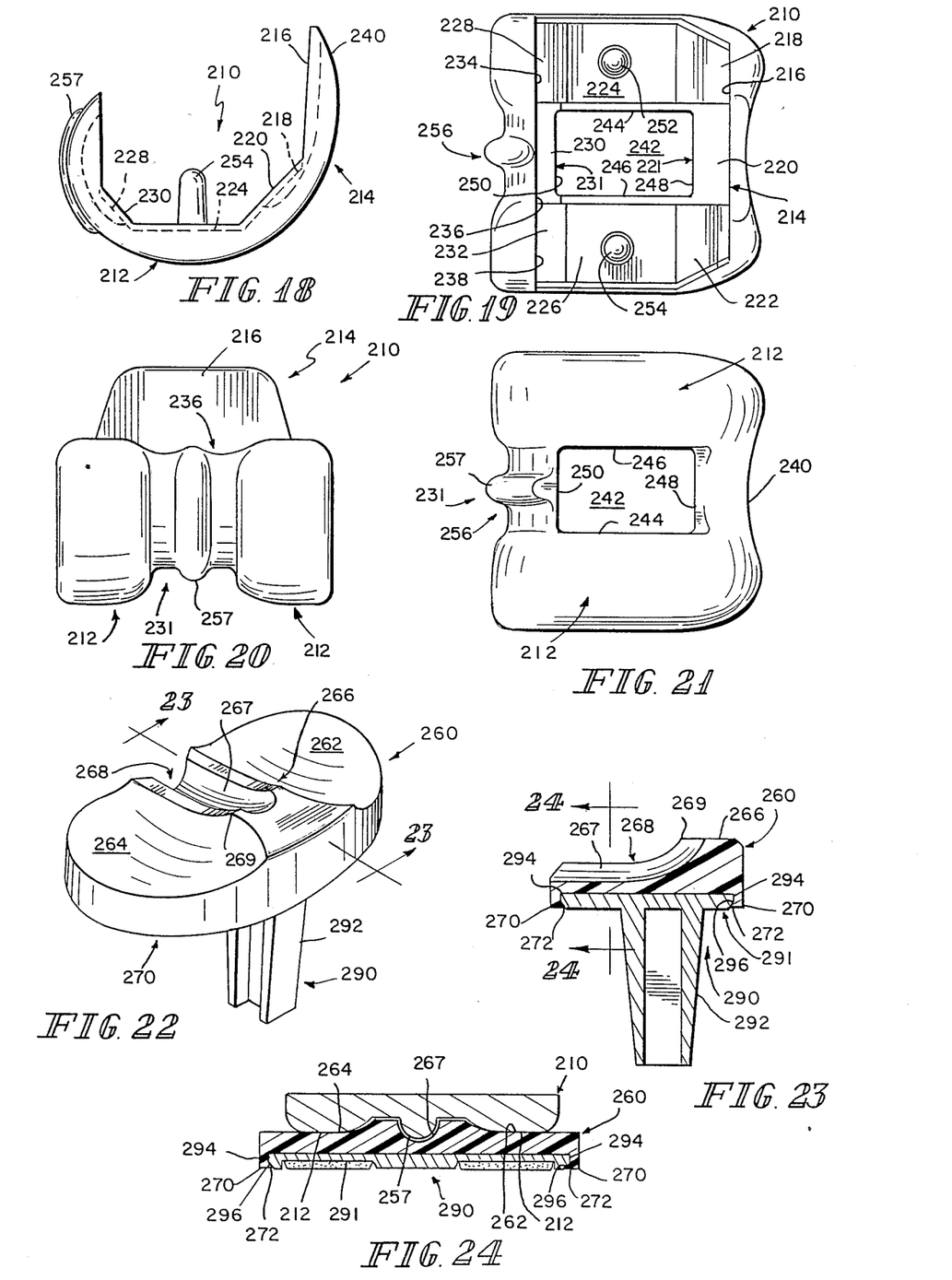
FIG. 18 shows a side view of a femoral component of a knee joint constructed in accordance with the present invention.
FIG. 19 shows a top plan view of the femoral component of FIG. 18.
FIG. 20 shows a rear or posterior view of the femoral component of FIGS. 18-19.
FIG. 21 shows a bottom plan view of the femoral component of FIGS. 18-20.
FIG. 22 shows a perspective view of a tibial insert and a tibial base formed in accordance with the present invention.
FIG. 23 shows a sectional view of the tibial insert and base of FIG. 22 taken along section line 23—23.
FIG. 24 shows a sectional view of the femoral component of FIGS. 18-21 received on the tibial insert and base of FIG. 23 taken along section line 24—24 of FIG. 23.

Surfaces 218 and 222 oppose anterior portions of condylar bearing portions 212, respectively Surfaces 224 and 226 oppose central portions of condylar bearing portions 212, while surfaces 228 and 234, and 232 and 238 oppose respective posterior portions of condylar bearing portions 212. Surface 220 is an interior surface of an anterior intercondylar portion 221 which extends between the anterior Portions of condylar bearing portions 212 Surface 220 may be slightly raised, as compared to surfaces 218 and 222, as shown in FIG. 18. Surfaces 230 and 236 are interior surfaces of posterior intercondylar portion 231 which extends between respective posterior portions of condylar bearing portions 212. Opposing interior surfaces 230 and 236 of posterior intercondylar portion 231 is exterior surface 256. Extending along exterior surface 256 of posterior intercondylar portion 231 is a ridge or runner 257. Ridge 257 runs parallel to and midway between condylar bearing portions 212.

Component 210 further comprises an intercondylar opening 242 which is defined by lateral edges 244 and 246 of condylar bearing portions 212, posterior edge 248 of anterior intercondylar portion 221, and anterior edge 250 of posterior intercondylar portion 231. These edges lie in substantially the same horizontal, or slightly convex, plan (as viewed in FIG. 18), such that no portion of the edges which form the side walls of opening 242 extend inwardly toward the femur beyond the interior surfaces of condylar bearing portions 212 and the other interior surfaces which define the contour of the distal cut. Accordingly, no additional resection of the femur is required to accommodate a femoral component which incorporates this feature. Femoral component 210 further comprises upwardly extending cylindrical posts 252 and 254 which fit into holes formed in the distal end of the femur to aid in firmly attaching component 210 to the femur. Femoral component 210 is preferably formed of a biologically compatible metal, such as a cobalt-chromium alloy or a titanium alloy.

FIGS. 22-24 show an assortment of views of a tibial insert 260 and a tibial base 290 for use with femoral component 210. Tibial insert 260 is preferably constructed of a biologically compatible high density polymer, such as ultra-high molecular weight polyethylene (UHMWPE).

Tibial insert 260 has two spaced-apart upwardly concave bearing surfaces 262 and 264 which will provide support for, and which will be in contact with, condylar bearing portions 212 of femoral component 210 in the implanted joint. In addition to bearing surfaces 262 and 264, the top surface of tibial insert 260 is provided with a relatively low intercondylar eminence 266 disposed between bearing surfaces 262 and 264, and a generally arcuately shaped (in cross-section) guide surface 268 on a posterior side of intercondylar eminence 266. Guide surface 268 extends upwardly along the posterior side of eminence 266 to a peak 269 which defines the highest portion of the tibial insert and which, when extended tangentially, forms an angle A of approximately 37° with the horizontal Guide surface 268 of intercondylar eminence 266 has a groove 267 formed therein midway between bearing surfaces 262 and 264 which extends laterally across a portion of tibial insert 260. Groove 267 receives ridge 257 of femoral component 210 and coacts therewith to prevent anterior dislocation of femoral component 210 as will be discussed in more detail later.

Tibial base 290 comprises a general planar platform 291 and a shank 292 extending downwardly from platform 291. Shank 292 illustratively comprises a tapered I-beam which is inserted into the tibia of the patient after the tibia has been resected to receive it.

Tibial insert 260 is illustratively formed by molding it about platform 291 of tibial base 290 such as by injection molding. Tibial insert 260 has a lower peripheral edge 270 which has a radially inwardly extending lip 272. Platform 291 of tibial base 290 has an outer perimetral edge 294 which has a radially inwardly and downwardly extending lower edge 296. Outer perimetral edge 294 of platform 291 of tibial base 290 is captured by lip 272 of tibial insert 260 when tibial insert 260 is molded about platform 291 of tibial base 290. Lip 272 of tibial insert 260 thus secures tibial insert 260 to tibial base 290.

FIG. 24 is a cross-section of femoral component 210, tibial insert 260 and tibial base 290 taken along line 24—24 of FIG. 23 wherein femoral component 210 is received on tibial insert 260 with the knee which is comprised of femoral component 210, tibial insert 260 and tibial base 290 in its fully extended position When the knee is flexed, femoral component 210 rotates on tibial insert 260 and ridge 257 of femoral component 210 rotatably slides in groove 267 of tibial insert 260. The coaction of ridge 257 and groove 267 reduces any anterior movement of femoral component 210 on tibial insert 260 as femoral component 210 rotates to the fully flexed Position of the knee. In contrast to the embodiment of FIGS. 1-17, femoral component 210 does not move posteriorly on tibial component 260 as it moves to the fully flexed position.

It should be understood that it is not necessary that the groove be formed in the guide surface 268 of tibial insert 260 and the ridge be provided on exterior surface 256 of posterior intercondylar portion 231 of femoral component 210. Alternately, the groove could be formed in exterior surface 256 of posterior intercondylar portion 231 of femoral component 210 and a ridge provided on guide surface 268 of tibial insert 260 and the same function of preventing anterior disclocation of femoral component 210 as the knee flexes be achieved.

From the preceding description of the preferred embodiments, it is evident that the objects of the invention are attained Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. A knee joint prosthesis, comprising:

a femoral component having a pair of spaced-apart condylar bearing portions, an anterior intercondylar portion, a posterior intercondylar portion, and an intercondylar opening between the anterior intercondylar portion and the posterior intercondylar portion, the posterior intercondylar portion having an exterior surface with a raised ridge thereon that extends along the exterior surface of the posterior intercondylar portion generally parallel to the spaced apart condylar bearing portions, the femoral components having an interior contour which closely matches an exterior contour of the end of the femur after the femur has been prepared to receive the femoral component, the interior contour of the femoral component being at least partially defined by generally horizontal superior surfaces of the condylar bearing portions and by the intercondylar opening, the intercondylar opening lying in a common plane with, and inferiorly to, said horizontal superior surfaces of the condylar bearing portions, a tibial component having a pair of spaced-apart bearing surfaces for supporting the condylar bearing portions of the femoral component and having an intercondylar portion including a posterior intercondylar portion between the bearing surfaces of the tibial component, the posterior intercondylar portion of the tibial component having a groove formed therein which extends therethrough generally parallel to the spaced-apart condylar bearing portions of the femoral component when the spaced-apart condylar bearing portions of the femoral component are supported by the bearing portions of the tibial component, wherein the ridge of the femoral component is received in the groove of the tibial component when the intercondylar bearing portions of the femoral component are supported on the bearing portions of the tibial component, the ridge rotatably slides in the groove when the knee flexes and the ridge and groove coact to reduce anterior movement of the femoral component as the knee flexes; and wherein the intercondylar portion of the tibial component does not extend all the way through the intercondylar opening of the femoral component.

2. A knee joint prosthesis, comprising:

a femoral component having a pair of spaced-apart condylar bearing portions, and anterior intercondylar portion, a posterior intercondylar portion, and an intercondylar opening between the anterior intercondylar portion and the posterior intercondylar portion, the femoral component having an interior contour which closely matches an exterior contour of the end of the femur after the femur has been prepared to receive the femoral component, the interior contour of the femoral component being at least partially defined by generally horizontal superior surfaces of the condylar bearing portions and by the intercondylar opening, the intercondylar opening lying in a common plane with, and inferiorly to, said horizontal superior surfaces of the condylar bearing portions, a tibial component having a pair of spaced-apart bearing surfaces for supporting the condylar bearing portions of the femoral component and an intercondylar portion including a posterior intercondylar portion, one of the posterior intercondylar portions of the femoral component and the tibial component having a raised ridge thereon which extends generally parallel to the condylar bearing portions of the femoral component, the other of the posterior intercondylar portions of the femoral component and the tibial component having a groove therein which extends generally parallel to the condylar bearing portions of the femoral component, wherein the ridge is received in the groove when the intercondylar bearing portions of the femoral component are supported on the bearing portions of the tibial component, the ridge rotating int eh groove when the knee flexes and the ridge and groove coacting to reduce anterior movement of the femoral component as the knee flexes, and wherein the intercondylar portion of the tibial component does not extend all the way through the intercondylar opening of the femoral component.

3. A knee joint prosthesis according to claim 1, wherein the ridge curves convexly along its longitudinal axis as it extends along the exterior surface of the intercondylar portion of the femoral component and the groove curves concavely along its longitudinal axis as it extends through the posterior intercondylar portion of the tibial component.

4. A knee joint prosthesis according to claim 1, wherein the tibial component comprises a tibial base and a tibial insert.

5. A knee joint prosthesis according to claim 4, wherein the tibial insert comprises a non-metallic pad having the spaced-apart bearing surfaces and the posterior intercondylar portion.

6. A knee joint prosthesis according to claim 5, wherein the tibial insert is formed by molding it about the tibial base.

7. A knee joint prosthesis according to claim 4 wherein the tibial base comprises a substantially planar platform portion for supporting the tibial insert, and a downwardly extending portion for insertion into an opening in the tibia to secure the platform portion to the tibia plateau.

8. A knee joint prosthesis according to claim 7, wherein the ridge and groove curve along their respective longitudinal axes in mating relation to each other.

9. A knee joint prosthesis according to claim 8, wherein the tibial component comprises a tibial base and a tibial insert.

10. A knee joint prosthesis according to claim 9, wherein the tibial insert comprises a non-metallic pad having the spaced-apart bearing surfaces and the posterior intercondylar portion.

11. A knee joint prosthesis according to claim 10, wherein the tibial insert is formed by molding it about the tibial base.

12. A knee joint prosthesis according to claim 9, wherein the tibial base comprises a substantially planar platform portion for supporting the tibial insert, and a downwardly extending portion for insertion into an opening in the tibia to secure the platform portion to the tibia plateau.

13. The knee joint of claim 1, wherein the femoral component and the tibial component are formed such that when the knee joint flexes the femoral component does not move posteriorly on the tibial component.

14. The knee joint of claim 7, wherein the femoral component and the tibial component are formed such that when the knee joint flexes the femoral component does not move posteriorly on the tibial component.

* * * * *